(12) United States Patent
Silber et al.

(10) Patent No.: US 10,821,130 B2
(45) Date of Patent: *Nov. 3, 2020

(54) OMEGA 3 FATTY ACIDS, NO RELEASING COMPOUND AND VITAMIN B12 AS NEUROPROTECTANT IN PATIENTS WITH NO DEMENTIA

(71) Applicant: NESTEC S.A., Vevey (CH)

(72) Inventors: Yvonne Beata Silber, Essertes (CH); Jeroen Antonius Johannes Schmitt, Moudon (CH); Corina Boschat, Lausanne (CH); Julie Hudry-Labbe, Epalinges (CH); Claus Rieker, St-Sulpice (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/336,308

(22) PCT Filed: Sep. 29, 2017

(86) PCT No.: PCT/EP2017/074729
§ 371 (c)(1),
(2) Date: Mar. 25, 2019

(87) PCT Pub. No.: WO2018/060395
PCT Pub. Date: Apr. 5, 2018

(65) Prior Publication Data
US 2019/0209601 A1  Jul. 11, 2019

Related U.S. Application Data

(60) Provisional application No. 62/401,443, filed on Sep. 29, 2016, provisional application No. 62/484,119, (Continued)

(51) Int. Cl.
*A61K 31/714* (2006.01)
*A61K 31/202* (2006.01)
(Continued)

(52) U.S. Cl.
CPC ............ *A61K 31/714* (2013.01); *A61K 31/14* (2013.01); *A61K 31/17* (2013.01); *A61K 31/197* (2013.01);
(Continued)

(58) Field of Classification Search
None
See application file for complete search history.

(56) References Cited

U.S. PATENT DOCUMENTS

2002/0182196 A1   12/2002   McCleary
2014/0271844 A1   9/2014    Miller
(Continued)

FOREIGN PATENT DOCUMENTS

WO   2010143053   12/2010
WO   2016207794   12/2016

OTHER PUBLICATIONS

ScienceDaily, Council for Responsible Nutrition, Nov. 9, 2010, pp. 1-3. (Year: 2010).*

(Continued)

*Primary Examiner* — Kyung S Chang
(74) *Attorney, Agent, or Firm* — K&L Gates LLP

(57) ABSTRACT

A method of attenuating, treating or preventing cognitive aging in an individual who does not have dementia includes administering to the individual a therapeutically effective amount of a composition containing an omega-3 fatty acid, a nitric oxide releasing compound, and Vitamin B12. The composition is administered in a daily dose that provides 50 to 500 times the recommended daily requirement (RDA) of Vitamin B12 per day, for example about 200 times the RDA (Continued)

of Vitamin B12 per day. Optionally Vitamin B6 and/or Vitamin B9 can be included in the composition. The method can achieve a benefit that is one or more of decreasing brain atrophy, increasing or maintaining number of synapses, increasing amyloid-β phagocytosis, or decreasing or maintaining neuroinflammation in the non-demented individual. The method can prevent dementia in an individual at risk thereof, for example an elderly human.

18 Claims, 1 Drawing Sheet

Related U.S. Application Data filed on Apr. 11, 2017, provisional application No. 62/484,156, filed on Apr. 11, 2017.

(51) Int. Cl.
| | |
|---|---|
| *A61K 31/4415* | (2006.01) |
| *A61K 31/519* | (2006.01) |
| *A61K 31/198* | (2006.01) |
| *A61P 43/00* | (2006.01) |
| *A61P 25/28* | (2006.01) |
| *A61K 31/14* | (2006.01) |
| *A61K 31/17* | (2006.01) |
| *A61K 31/375* | (2006.01) |
| *A61K 31/4406* | (2006.01) |
| *A61K 33/00* | (2006.01) |
| *A61K 31/197* | (2006.01) |
| *A61K 31/341* | (2006.01) |
| *A61K 31/355* | (2006.01) |
| *A61K 31/4188* | (2006.01) |
| *A61K 31/455* | (2006.01) |
| *A61K 31/51* | (2006.01) |
| *A61K 31/525* | (2006.01) |
| *A61K 31/59* | (2006.01) |
| *A61K 31/675* | (2006.01) |
| *A61K 33/04* | (2006.01) |

(52) U.S. Cl.
CPC .......... *A61K 31/198* (2013.01); *A61K 31/202* (2013.01); *A61K 31/341* (2013.01); *A61K 31/355* (2013.01); *A61K 31/375* (2013.01); *A61K 31/4188* (2013.01); *A61K 31/4406* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/59* (2013.01); *A61K 31/675* (2013.01); *A61K 33/00* (2013.01); *A61K 33/04* (2013.01)

(56) References Cited

U.S. PATENT DOCUMENTS

2015/0086625 A1   3/2015  Miller
2016/0367509 A1*  12/2016 Pan ................. A23K 20/158

OTHER PUBLICATIONS

Oulhaj et al., "Omega-3 fatty acid status enhances the prevention of cognitive decline by B vitamins in mild cognitive impairment", Journal of Alzheimer's Disease, vol. 50 (2016), pp. 547-557. (Year: 2016).*

Hughes et al., "Vitamin B12 and ageing: current issues and interaction with folate", Review Article, Annals of Clinical Biochemistry 50 (4) 2013, pp. 315-329 (Year: 2013).*

Sindi et al., "The CAIDE dementia risk score app: the development of an evidence-based mobile application to predict the risk of dementia," Alzheimer's & Dementia: Diagnosis, Assessment & Disease Monitoring 1 (2015), pp. 328-333. (Year: 2015).*

* cited by examiner

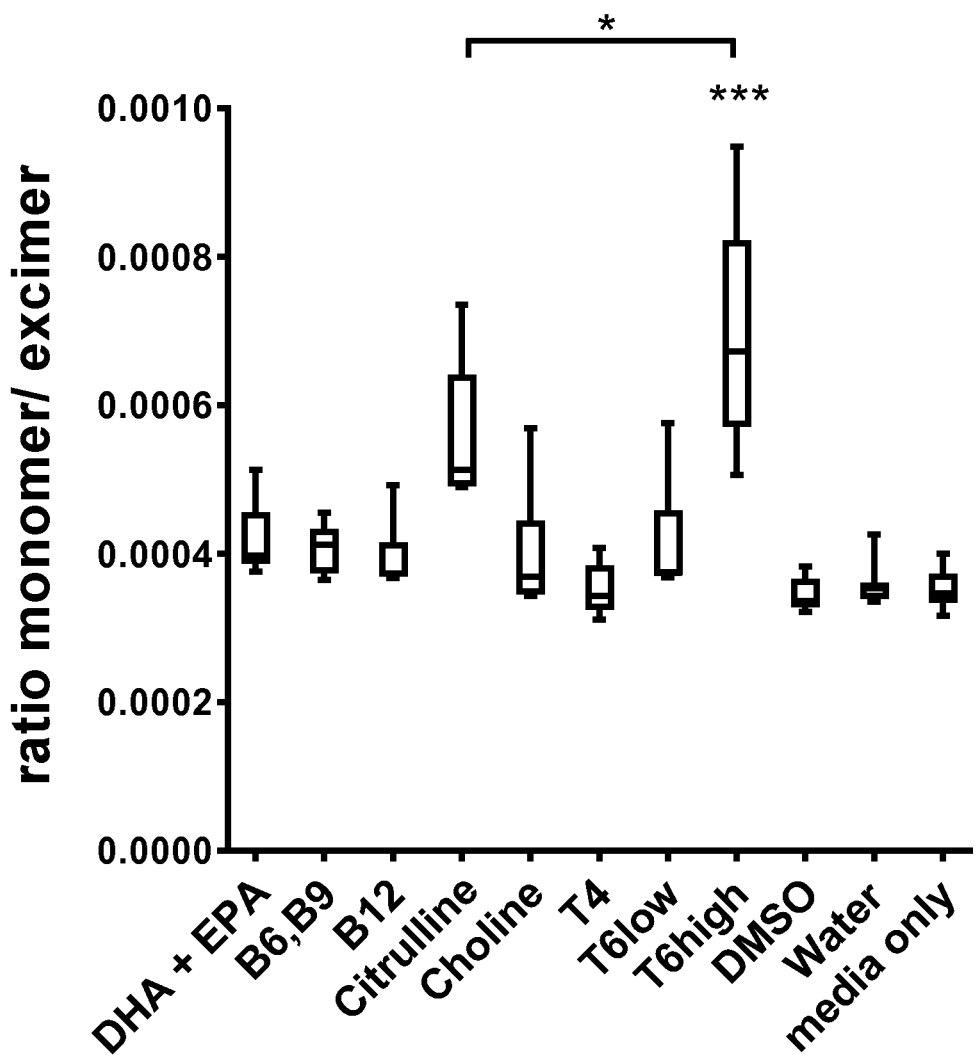

OMEGA 3 FATTY ACIDS, NO RELEASING COMPOUND AND VITAMIN B12 AS NEUROPROTECTANT IN PATIENTS WITH NO DEMENTIA

CROSS REFERENCE TO RELATED APPLICATIONS

The present application is a National Stage of International Application No. PCT/EP2017/074729, filed on Sep. 29, 2017, which claims priority to U.S. Provisional Application No. 62/401,443, filed on Sep. 29, 2016, U.S. Provisional Application No. 62/484,119, filed on Apr. 11, 2017, and U.S. Provisional Application No. 62/484,156, filed on Apr. 11, 2017, the entire contents of which are being incorporated herein by reference.

BACKGROUND

The present disclosure generally relates to compositions and methods that attenuate cognitive aging in individuals who do not have dementia. More specifically, the present disclosure relates to attenuating cognitive aging by administering a composition comprising a combination of an omega-3 fatty acid, a nitric oxide releasing compound, and a high amount of Vitamin B12.

Population aging has been a remarkable demographic event. As the growth of the older population has outpaced the total population due to increased longevity, the proportion of older persons relative to the rest of the population has increased considerably due to decreased fertility rates. For example, one in every twelve individuals was at least 60 years of age in 1950, and one in every ten was aged 60 years or older by the end of 2000. By the end of 2050, the number of persons worldwide that is 60 years or over is projected to be one in every five.

Aged or aging individuals frequently suffer some degree of cognitive impairment, including decline in cognitive function that progresses with age; and age-related changes in brain morphology and cerebrovascular function are commonly observed. Cognitive decline has been consistently reported with aging across a range of cognitive domains including processing speed, attention, episodic memory, spatial ability and executive function. Brain imaging studies have revealed that these normal age-related cognitive declines are associated with decreases in both grey and white matter volume in the brain, with the fronto-striatal system most heavily compromised with aging. These decreases in cortical volume can be attributed to a number of detrimental cellular processes involved with normal aging, such as accumulation of damage by free radicals over time leading to oxidative damage, chronic low-grade inflammation, homocysteine accumulation (which when elevated are a risk factor for cognitive impairment and dementia), and decreased mitochondrial efficiency. In addition to direct cellular damage, the brain is also indirectly impaired by insults to micro-vascular structures. It is evident that the pathology of aging and also dementia involves a complexity of these interacting factors, which are linked together. For example, mitochondrial dysfunction leads to increased oxidative stress, and oxidative stress can trigger inflammation and vascular insults.

Furthermore, cognitive decline is an early predictor for Alzheimer pathology and begins before the onset of dementia. In this context, the cognitive composite score represents a reliable means to assess the cognitive decline preceding dementia. Considerable evidence suggests that maintaining brain health and preventing cognitive decline with advancing age may prevent or delay development of dementia due to Alzheimer's disease and other aged related neuropathologies.

Nutrition, education, physical exercise and cognitive exercise have been recently demonstrated as possible intervention to prevent cognitive decline with aging. An abundance of clinical, epidemiological, and individual evidence is in favor of individual nutritional factors that reduce dementia risk and age-related neurodegeneration. However, formal trial testing of nutritional interventions has yielded mixed results (Schmitt et al., Nutrition Reviews 68: S2-S5 (2010).

Several long term studies have failed to observe any cognitive benefits with interventions using combinations of B6, B12 and folate. McMahon et al. (2006) N Engl J Med, 354(26), 2764-2772, found no effect on cognition in adults aged 65+ after 2 years consumption of a supplement containing folate (1000 µg), Vitamin B12 (500 µg) and B6 (10 mg). Similarly, Hankey et al. (2013) (Stroke, 44(8), 2232-2239) found that daily supplementation with folic acid (2000 µg), Vitamin B6 (25 mg), and Vitamin B12 (500 µg), to cognitively unimpaired patients with previous stroke or transient ischemic attack, lowered mean tHcy but had no effect on the incidence of cognitive impairment or cognitive decline, as measured by the MMSE, during a median of 2.8 years.

Several short-term studies have also failed to show an effect of the combination of B6, B12 and folate for improving cognitive function. Lewerin et al. (2005) Am J Clin Nutr, 81(5), 1155-1162, found that 4 months of supplementation of folic acid (800 µg), Vitamin B12 (500 µg), and Vitamin B6 (3 mg) had no effect on cognition in older adults (median age 76 years).

SUMMARY

Without being bound by theory, the present inventors believe that prior nutritional interventions attempting to reduce dementia risk and age-related neurodegeneration have focused on the administration of nutrients in isolation rather than together intelligently in combination to catapult the magnitude of effect by nutrient interaction. Moreover, studies investigating the effects of combined ingredients on cognitive function have used a mixture of constituents that all target the same mechanism (e.g. a mix of folate, B12, B6 mix targeting Hcy levels, or a mix of Vitamins C and E targeting oxidative damage), which may be why this evidence is as inconsistent as the single ingredient research. Therefore, the present disclosure is generally directed to a multi-intervention approach whereby each of the nutritional interventions targets a different risk factor associated with cognitive decline.

Accordingly, in a general embodiment, the present disclosure provides a method of attenuating, treating or preventing cognitive aging in a non-demented individual in need thereof or at risk thereof. The method comprises administering to the individual a therapeutically effective amount of a composition comprising an omega-3 fatty acid, a nitric oxide releasing compound, and Vitamin B12. The composition is administered in a daily dose that provides 50 to 500 times the recommended daily requirement (RDA) of Vitamin B12 per day.

In a more preferred embodiment, the daily dose provides about 200 times the RDA of the Vitamin B12 per day, e.g.

between 100 and 300 times or preferably between 150 and 250 times the recommended daily requirement (RDA) of Vitamin B12 per day.

In an embodiment, the individual is an older adult, for example an elderly human.

In an embodiment, the individual has a low DHA status at baseline. In an embodiment, the individual has a Clinical Dementia Rating (CDR) of 0.5 at baseline. In an embodiment the individual has a plasma homocysteine level at baseline of at least 12 µmol/L. In an embodiment, the individual has a risk score in Cardiovascular Risk Factors, Aging and Dementia (CAIDE) of 10 to 15 at baseline. In an embodiment, the individual is amyloid positive on amyloid PET scans at baseline. In an embodiment, the individual has a genotype indicating risk of cognitive decline.

In an embodiment, the composition is orally administered to the individual daily for at least one month.

In an embodiment, the nitric oxide releasing compound comprises citrulline.

In an embodiment, the omega-3 fatty acid comprises a fatty acid selected from the group consisting of docosahexaenoic acid, eicosapentaenoic acid and mixtures thereof.

In an embodiment, the composition comprises one or more additional B vitamins selected from the group consisting of Vitamin B1, Vitamin B2, Vitamin B3, Vitamin B5, Vitamin B6, Vitamin B7 and Vitamin B9; preferably at least Vitamin B6 and/or Vitamin B9, more preferably all of Vitamin B1, Vitamin B2, Vitamin B3, Vitamin B5, Vitamin B6, Vitamin B7 and Vitamin B9.

In an embodiment, the composition comprises one or more antioxidants selected from the group consisting of Vitamin C, Vitamin D, Vitamin E, selenium and choline, preferably choline bitartrate.

In another embodiment, the present disclosure provides a method of attenuating, treating or preventing cognitive aging in a non-demented individual in need thereof or at risk thereof, the method comprising administering to the individual a therapeutically effective amount of a composition comprising an omega-3 fatty acid, a nitric oxide releasing compound, and Vitamin B12, and the composition is administered in a daily dose that provides about 0.4 mg to about 1.0 mg of the Vitamin B12 per day.

In another embodiment, the present disclosure provides a method of achieving one or more of benefits selected from the group consisting of decreasing brain atrophy, increasing or maintaining number of synapses, increasing or maintaining amyloid-β phagocytosis, and decreasing neuroinflammation in a non-demented individual in need thereof. The present disclosure also provides a method of achieving one or more of the benefits selected from the group consisting of improvement of neuronal fluidity, stimulation of neuronal plasticity and activity, improvement of the anti-inflammatory potential, reduction of reactive oxygen species (ROS) and/or target NO release. The present disclosure also provides a method of achieving one or more of the benefits selected from support or maintenance of cognitive performance, support or maintenance of brain performance, slowing down aging of the brain, support of an active mind and brain fitness, support or maintenance of a healthy brain, enhancement of memory, enhancement of executive functions, enhancement of attention, maintenance of cognitive health, maintenance of brain cellular health, etc. Any of such benefits may be preferably achieved by a method as defined herein, preferably a method of attenuating, treating or preventing cognitive aging in a non-demented individual in need thereof or at risk thereof. The methods comprise administering to the individual a therapeutically effective amount of a composition comprising an omega-3 fatty acid, a nitric oxide releasing compound, and Vitamin B12, Vitamin B12 preferably in an amount as described herein. The composition is typically administered in a daily dose that provides 50 to 500 times the recommended daily requirement (RDA) of Vitamin B12 per day, as defined herein. The daily dose can provide about 200 times the RDA of Vitamin B12 per day, e.g. between 100 and 300 times or preferably between 150 and 250 times the recommended daily requirement (RDA) of Vitamin B12 per day. The nitric oxide releasing compound can comprise citrulline, and the omega-3 fatty acid can comprise a fatty acid selected from the group consisting of docosahexaenoic acid, eicosapentaenoic acid and mixtures thereof.

In another embodiment, the present disclosure provides a composition comprising a combination of an omega-3 fatty acid, a nitric oxide releasing compound, and Vitamin B12. A daily dose of the composition provides 50 to 500 times the recommended daily requirement (RDA) of Vitamin B12 per day, as defined herein. The composition comprises the combination in an amount effective to attenuate cognitive aging in a non-demented individual. The composition can be a food product comprising an ingredient selected from the group consisting of protein, carbohydrate, fat and combinations thereof. The composition can be a pharmaceutical composition comprising a component selected from the group consisting of pharmaceutically acceptable carriers, diluents and excipients.

In another embodiment, the present disclosure provides a method of making a food composition for attenuating cognitive aging in a non-demented individual. The method comprises adding an effective amount of a combination of an omega-3 fatty acid, a nitric oxide releasing compound, and Vitamin B12 to at least one ingredient selected from the group consisting of protein, carbohydrate, and fat. A daily dose of the food composition provides 50 to 500 times the recommended daily requirement (RDA) of Vitamin B12 per day, as defined herein.

In another embodiment, the present disclosure provides a method of making a pharmaceutical composition for attenuating cognitive aging in a non-demented individual, the method comprising adding an effective amount of a combination of an omega-3 fatty acid, a nitric oxide releasing compound, and Vitamin B12 to at least one component selected from the group consisting of pharmaceutically-acceptable carriers, diluents and excipients. A daily dose of the pharmaceutical composition provides 50 to 500 times the recommended daily requirement (RDA) of Vitamin B12 per day as defined herein.

In another embodiment, the present disclosure provides a method of preventing dementia in an individual at risk thereof. The method comprises administering to the individual a therapeutically effective amount of a composition comprising an omega-3 fatty acid, a nitric oxide releasing compound, and Vitamin B12. The composition is administered in a daily dose that provides 50 to 500 times the recommended daily requirement (RDA) of Vitamin B12 per day as defined herein. The daily dose can provide about 200 times the RDA of the Vitamin B12 per day, e.g. between 100 and 300 times or preferably between 150 and 250 times the recommended daily requirement (RDA) of Vitamin B12 per day. The dementia that is prevented can be selected from the group consisting of Alzheimer's disease, vascular dementia, Lewy body dementia, frontotemporal dementia, and combinations thereof.

In another embodiment, the present disclosure provides a method of improving cognitive ability in a non-demented individual (e.g., an individual in need thereof), the method comprising administering to the individual a therapeutically effective amount of a composition comprising an omega-3 fatty acid, a nitric oxide releasing compound, and Vitamin B12, and the composition is administered in a daily dose that provides 50 to 500 times the recommended daily requirement (RDA) of Vitamin B12 per day, preferably as defined herein before.

An advantage of one or more embodiments provided by the present disclosure is to attenuate cognitive aging in non-demented individuals such as an elderly human.

Another advantage of one or more embodiments provided by the present disclosure is to use omega-3 fatty acids such as docosahexaenoic acid (DHA) and eicosapentaenoic acid (EPA) to modulate neuronal membrane fluidity, stimulate neuroplasticity, provide anti-neuroinflammatory effects, and/or reduce brain oxidative stress, in combination with B vitamins such as B12 to decrease homocysteine levels in the plasma and with a nitric-oxide releasing compound such as arginine or citrulline to protect signal transduction pathways.

Yet another advantage of one or more embodiments provided by the present disclosure is to use a higher amount of Vitamin B12 relative to known nutritional interventions for cognitive aging.

Still another advantage of one or more embodiments provided by the present disclosure is to decrease brain atrophy and neuroinflammation and to increase or maintain amyloid-β phagocytosis and the number of synapses in a non-demented individual. In this context, one or more of the benefits achieved hereby are selected from the group consisting of improvement of neuronal fluidity, stimulation of neuronal plasticity and activity, improvement of the anti-inflammatory potential, reduction of reactive oxygen species (ROS), and/or target NO release or from other benefits described herein.

Additional features and advantages are described herein and will be apparent from the following FIGURE and Detailed Description.

BRIEF DESCRIPTION OF THE FIGURES

FIG. 1 is a graph showing the results from membrane fluidity studies of Example 3. As can be seen in FIG. 1 DHA+EPA in combination with high B12 and citrulline ($T6_{high}$) strongly increases membrane fluidity.

DETAILED DESCRIPTION

Definitions

Some definitions are provided hereafter. Nevertheless, definitions may be located in the "Embodiments" section below, and the above header "Definitions" does not mean that such disclosures in the "Embodiments" section are not definitions.

All percentages expressed herein are by weight of the total weight of the composition unless expressed otherwise. As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a component" or "the component" includes two or more components.

The words "comprise," "comprises" and "comprising" are to be interpreted inclusively rather than exclusively. Likewise, the terms "include," "including" and "or" should all be construed to be inclusive, unless such a construction is clearly prohibited from the context. Nevertheless, the compositions disclosed herein may lack any element that is not specifically disclosed herein. Thus, a disclosure of an embodiment using the term "comprising" includes a disclosure of embodiments "consisting essentially of" and "consisting of" the components identified. A composition "consisting essentially of" contains at least 50 wt. % of the referenced components, preferably at least 75 wt. % of the referenced components, more preferably at least 85 wt. % of the referenced components, most preferably at least 95 wt. % of the referenced components.

The term "and/or" used in the context of "X and/or Y" should be interpreted as "X," or "Y," or "X and Y". Where used herein, the terms "example" and "such as", particularly when followed by a listing of terms, are merely exemplary and illustrative and should not be deemed to be exclusive or comprehensive.

The terms "food," "food product" and "food composition" mean a product or composition that is intended for ingestion by an individual such as a human and provides at least one nutrient to the individual. The compositions of the present disclosure, including the many embodiments described herein, can comprise, consist of, or consist essentially of the elements disclosed herein, as well as any additional or optional ingredients, components, or elements described herein or otherwise useful in a diet.

"Prevention" includes reduction of risk and/or severity of a condition or disorder. The terms "treatment," "treat," "attenuate" and "alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder, and include treatment of patients at risk of contracting a disease or suspected to have contracted a disease, as well as patients who are ill or have been diagnosed as suffering from a disease or medical condition. The term does not necessarily imply that a subject is treated until total recovery. These terms also refer to the maintenance and/or promotion of health in an individual not suffering from a disease but who may be susceptible to the development of an unhealthy condition. These terms are also intended to include the potentiation or otherwise enhancement of one or more primary prophylactic or therapeutic measure. The terms "treatment," "treat," "attenuate" and "alleviate" are further intended to include the dietary management of a disease or condition or the dietary management for prophylaxis or prevention a disease or condition. A treatment can be patient- or doctor-related.

The term "individual" means any animal, including humans, that could suffer from cognitive aging and thus benefit from one or more of the methods disclosed herein.

Generally, the individual is a human or an avian, bovine, canine, equine, feline, hicrine, lupine, murine, ovine or porcine animal. A "companion animal" is any domesticated animal, and includes, without limitation, cats, dogs, rabbits, guinea pigs, ferrets, hamsters, mice, gerbils, horses, cows, goats, sheep, donkeys, pigs, and the like. Preferably, the individual is a human or a companion animal such as a dog or cat, most preferably a human.

The term "elderly" in the context of a human means an age from birth of at least 60 years, preferably above 63 years, more preferably above 65 years, and most preferably above 70 years. The term "older adult" in the context of a human means an age from birth of at least 45 years, preferably above 50 years, more preferably above 55 years, and includes elderly individuals.

For other animals, an "older adult" has exceeded 50% of the average lifespan for its particular species and/or breed within a species. An animal is considered "elderly" if it has surpassed 66% of the average expected lifespan, preferably if it has surpassed the 75% of the average expected lifespan, more preferably if it has surpassed 80% of the average expected lifespan. An elderly cat or dog has an age from birth of at least about 7 years.

"Cognitive aging" is a decline in cognitive ability that progresses with age, for example an elderly age that is increasing, and can include age-related changes in brain morphology and/or cerebrovascular function. Cognitive aging does not include impaired cognitive ability caused by an underlying condition other than aging, such as a head injury or depression.

"Cognitive ability" is defined as the intellectual process by which an individual becomes aware of, perceives, or comprehends ideas. Cognitive ability embraces the quality of knowing, which includes all aspects of perception, recognition, conception, sensing, thinking, reasoning, remembering and imaging. Loss of cognitive ability is the difficulty in dealing with or reacting to new information or situations. Cognitive impairment may manifest itself in many ways, e.g., short-term memory loss, diminished capacity to learn, diminished rate of learning, diminished attention, diminished motor performance, and/or dementia, among other indicia. Non-limiting examples of specific cognitive domains that include abilities that decrease with age are (i) attention: processing speed, and selected and divided attention; (ii) learning and memory: delayed free recall, source memory, prospective memory, and episodic memory; (iii) language: verbal fluency, visitation naming, and word finding; (iv) visuospatial abilities: visual construction skills; and (v) executive functioning: planning, decision making, reasoning, and mental flexibility.

As used herein, an "effective amount" is an amount that prevents a deficiency, treats a disease or medical condition in an individual or, more generally, reduces symptoms, manages progression of the diseases or provides a nutritional, physiological, or medical benefit to the individual. The relative terms "improved," "increased," "enhanced" and the like refer to the effects of the composition disclosed herein relative to a composition lacking one or more ingredients and/or having a different amount of one or more ingredients, but otherwise identical.

EMBODIMENTS

In an aspect of the present disclosure, a composition comprises a combination of an omega-3 fatty acid, a nitric oxide releasing compound, and B vitamins providing a high amount of Vitamin B12; and preferably the composition comprises the combination in an amount effective to attenuate cognitive aging and/or improve cognitive ability in a non-demented individual. Such compositions preferably have high Vitamin B12 levels as defined above. In another aspect, a method for attenuating cognitive aging and/or improving cognitive ability in a non-demented individual comprises administering (e.g., orally) an effective amount of the composition to the individual. The composition is preferably as defined herein.

The composition can increase cognitive function in a non-demented individual susceptible to or suffering from a decline in cognitive function brought about by the aging process. The composition can prevent, reduce or delay a decline in cognitive function in a non-demented individual susceptible to or suffering from a decline in cognitive function brought about by the aging process. In some embodiments, the methods comprise, prior to the administration, identifying the individual as having cognitive aging or being at risk of the cognitive aging. For example, the methods can comprise, prior to the administration, identifying the individual as being in need of improved cognitive ability. The composition can decrease brain atrophy and neuroinflammation and increase amyloid-β phagocytosis and the number of synapses.

For example, the present disclosure provides a method of treating cognitive aging in a non-demented individual in need thereof (e.g., having cognitive aging), the method comprising administering to the individual a therapeutically effective amount of a composition comprising an omega-3 fatty acid, a nitric oxide releasing compound, and a high amount of Vitamin B12. As another example, the present disclosure provides a method of preventing cognitive aging in a non-demented individual at risk thereof (e.g., an older adult or an elderly individual but not yet having cognitive aging), the method comprising administering to the individual a therapeutically effective amount of a composition comprising an omega-3 fatty acid, a nitric oxide releasing compound, and a high amount of Vitamin B12 as defined herein. As yet another example, the present disclosure provides a method of improving cognitive ability in a non-demented individual (e.g., an individual in need thereof), the method comprising administering to the individual a therapeutically effective amount of a composition comprising an omega-3 fatty acid, a nitric oxide releasing compound, and a high amount of Vitamin B12. Such compositions are preferably as defined above and preferably have high Vitamin B12 levels as defined above.

A "non-demented" individual has a Clinical Dementia Rating of up to 0.5. The CDR measures dementia severity and is a global rating of dementia with scores ranging from 0 to 3 (0, 0.5, 1, 2, and 3) rated by a semi-structured subject and informant interview. Hughes et al., Br. J. Psychiatry 140:566-72 (1982). A clinician synthesizes the cognitive and functional abilities based on six domains, including memory, orientation, judgment and problem solving, community affairs, home and hobbies, and personal care. The scale has good inter-rater agreement.

The non-demented individual does not have any of Alzheimer's disease, vascular dementia, Lewy body dementia, or frontotemporal dementia. In some embodiments, the non-demented individual is a healthy aging individual. In other embodiments, the non-demented individual has a phenotype associated with age-related cognitive impairment. For example, when compared to a control individual not having the phenotype, the non-demented individual may have a phenotype that includes one or more of decreased ability to recall, short-term memory loss, decreased learning rate, decreased capacity for learning, decreased problem solving skills, decreased attention span, decreased motor performance, or increased confusion.

A non-limiting example of a non-demented individual at risk of cognitive aging is a human with spontaneous memory complaints but who nevertheless has a Mini Mental State Examination (MMSE) score of at least 24 and has independence in basic daily activities as shown by an Activities of Daily Living (ADL) score of at least 4. An MMSE score for the present purpose may be e.g. 24 to 30, more preferably 26 to 30.

The MMSE is a very brief, easily administered/executed mental status examination that has proved to be a highly reliable and valid instrument for detecting and tracking the progression of the cognitive impairment associated with neurodegenerative diseases. The MMSE is a fully structured scale that consists of 30 points grouped into seven categories: orientation to place (state, county, town, hospital, and floor), orientation to time (year, season, month, day, and date), registration (immediately repeating three words), attention and concentration (serially subtracting 7, beginning with 100, or, alternatively, spelling the word world backward), recall (recalling the previously repeated three words), language (naming two items, repeating a phrase, reading aloud and understanding a sentence, writing a sentence, and following a three-step command), and visual construction (copying a design). Folstein et al., J. Psychiat. Res. 12:189-198 (1975).

The MMSE is scored in terms of the number of correctly completed items; lower scores indicate poorer performance and greater cognitive impairment. The total score ranges from 0 to 30.

The ADL is an informant-based activity of daily living scale widely used measure to assess activities of daily living in people with and without AD. The instrument assesses ability over a wide range of performances. The ADL has shown sensitivity to change among mildly impaired individuals compared to non-impaired controls and can capture functional changes. Galasko et al., Alzheimer Dis. Assoc. Disord. 11 Suppl. 2:S33-9 (1997).

As noted earlier herein, considerable evidence suggests that maintaining brain health and preventing cognitive decline with advancing age may prevent or delay development of dementia. Therefore, the methods disclosed herein which treat or prevent cognitive aging can also ultimately prevent dementia such as Alzheimer's disease. Accordingly, another aspect of the present disclosure is a method of preventing dementia in an individual at risk thereof. The method comprises administering to the individual a therapeutically effective amount of the composition disclosed herein. The dementia that is prevented can be selected from the group consisting of Alzheimer's disease, vascular dementia, Lewy body dementia, frontotemporal dementia, and combinations thereof. The methods preferably comprise administering compositions as described herein.

In an embodiment, the individual has a low DHA status (erythrocyte omega 3 index<4.8%) at baseline. In an embodiment, the individual has a Clinical Dementia Rating (CDR) of 0.5 at baseline. In an embodiment, the individual has a high plasma homocysteine level at baseline. As used herein, a "high" plasma homocysteine level is plasma homocysteine of at least 12 µmol/L. In another embodiment, the individual has a CAIDE (Cardiovascular Risk Factors, Aging and Dementia) risk score of 10-15 at baseline. In yet another embodiment, the individual is amyloid positive on amyloid PET scans at baseline. In yet another embodiment, the individual has a genotype indicating risk of cognitive decline (e.g., Apolipoprotein E (APOE) genotype).

A daily dose of the composition can provide 0.1 to 600 times, e.g. 0.1 to 500 times, 0.1 to 40 times, 0.1 to 50 times, or 50 to 600 times the recommended daily requirement (RDA) of Vitamin B12 Such dosages may preferably include 100 to 500 times the RDA of Vitamin B12, more preferably 150 to 300 times the RDA of Vitamin B12, even more preferably 150 to 250 times the RDA of Vitamin B12, and most preferably about 200 times the RDA of Vitamin B12. Further in this regard, the United States RDA of Vitamin B12 is 2.4 micrograms daily for humans of age 14 years and older, so such individuals may be administered a daily dose of the composition that provides 0.1 mg to 1.5 mg of Vitamin B12 per day, preferably 0.2 mg to 1.2 mg of Vitamin B12 per day, more preferably 0.4 mg to 1.0 mg of Vitamin B12 per day, and most preferably about 0.5 mg of Vitamin B12 per day.

In various embodiments, the omega-3 fatty acid is 1 to 50 wt. % of the composition, preferably 1 to 30 wt. % of the composition, and most preferably 1 to 15 wt. % of the composition. Preferably, the omega-3 fatty acid comprises at least one of eicosapentaenoic acid (EPA) or docosahexaenoic acid (DHA) and more preferably comprises both EPA and DHA, each of which has anti-inflammatory properties. A daily dose of the composition preferably provides 0.5 g to 1.0 g of DHA per day and/or 0.5 g to 1.0 g of EPA per day, more preferably 0.7 g to 1.0 g of DHA per day and/or 0.6 mg to 0.75 g of EPA per day, and most preferably about 770 mg of DHA per day and/or about 700 mg of EPA per day.

The omega-3 fatty acid may comprise a blend of one or more sources of omega-3 fatty acids, and each of the one or more sources of omega-3 fatty acids can be natural (e.g., fish oil) or synthetic (i.e., formed through a chemical process manipulated by a human, as opposed to those of natural origin). The term "fish oil" means a crude or purified fatty or oily extract rich in omega-3 fatty acids and obtained from a sea individual, preferably a cold-water fish such as, but not limited to, salmon, tuna, mackerel, herring, sea bass, striped bass, halibut, catfish, and sardines, as well as shark, shrimp, and clams, or any combination thereof.

The nitric oxide releasing compound is any compound or compounds that cause or can result in the release of nitric oxide in an individual. The nitric oxide releasing compound preferably comprises one or more of arginine, citrulline, ornithine, or a peptide or protein containing at least one of these amino acids, preferable arginine and/or citrulline, and even more preferably comprises citrulline, which provides beneficial effects on the cardiovascular system, specifically in terms of improving blood flow, endothelial function and blood pressure. In various embodiments, the nitric oxide releasing compound is 1 to 20 wt. % of the composition, preferably 1 to 15 wt. % of the composition, and more preferably 1 to 10 wt. % of the composition. In an embodiment, a daily dose of the composition provides from 0.5 g to 10.0 g of the nitric oxide releasing compound (e.g., citrulline) per day, preferably 1.0 g to 5.0 g per day, more preferably 2.0 g to 4.0 g per day, and most preferably about 3.0 g per day.

The B vitamins can further comprise other B vitamins additional to the Vitamin B12, for example one or more of Vitamin B1 (thiamine), Vitamin B2 (riboflavin), Vitamin B3 (niacin), Vitamin B5 (pantothenic acid), Vitamin B6 (pyridoxine), Vitamin B7 (biotin) and Vitamin B9 (Folic acid) or salts, conjugates or derivatives thereof that have B vitamin activity. The composition can comprise from 0.1 to 40 times the RDA of one or more of these additional B vitamins, preferably 1 to 20 times the RDA, and more preferably 1 to 10 times the RDA.

In an embodiment, the B vitamins further comprise at least Vitamin B6 additional to the Vitamin B12. In an embodiment, the B vitamins further comprise at least Vitamin B9 additional to the Vitamin B12. In a preferred embodiment, the B vitamins further comprise at least both Vitamin B6 and Vitamin B9 additional to the Vitamin B12. In a most preferred embodiment, the B vitamins further comprise all of Vitamin B1 (thiamine), Vitamin B2 (riboflavin), Vitamin B3 (niacin), Vitamin B5 (pantothenic acid), Vitamin B6 (pyridoxine), Vitamin B7 (biotin) and Vitamin B9 (Folic acid), additional to the Vitamin B12.

The composition can comprise from 0.1 to 40 times the RDA of the Vitamin B6 and/or the Vitamin B9, preferably 1 to 20 times the RDA, and more preferably 1 to 10 times the RDA. For example, a daily dose of the composition can provide 15 mg to 25 mg of the Vitamin B6 per day, preferably 15 mg to 20 mg of the Vitamin B6 per day, most preferably about 18 mg of the Vitamin B6 per day. A daily dose of the composition can provide 0.1 mg to 1.0 mg of the Vitamin B9 per day, preferably 0.3 mg to 0.8 mg of the Vitamin B9 per day, most preferably about 0.4 mg of the Vitamin B9 per day. Each of Vitamins B6, B9 and B12 has the ability to decrease homocysteine levels in the plasma.

In some embodiments, the composition can further comprise one or more antioxidants to protect against oxidative damage and inflammation-induced damage. Non-limiting examples of suitable antioxidants include Vitamin C, Vitamin D, Vitamin E, selenium and choline, preferably choline bitartrate, and combinations thereof. The composition can comprise 0.0001 wt. % to 25 wt. % of the antioxidant, if present; preferably 0.0001 wt. % to about 15 wt. %; more preferably 0.001 wt. % to 5 wt. %; and most preferably 0.001 wt. % to 2 wt. %.

The choline can be provided by an ingredient selected from the group consisting of choline chloride, choline bitartrate, citicoline (CDP-choline), L-alpha-glycerophosphocholine (Alpha-GPC), lecithin, phosphatidylcholine, and mixtures thereof. Moreover, the composition can be administered to the individual in a daily dose that provides 5.5 mg/day to 5,500 mg/day of the choline. In this context, the composition may be administered to the individual in a daily dose that provides 0.01 to 10.0 times the recommended daily requirement (RDA) of the choline, for example 0.15 to 6.0 times the RDA of the choline. In this regard, the RDA of choline is 550 mg/day, and thus the composition can be administered in a daily dose that provides 5.5 mg/day to 5,500 mg/day of the choline, for example 85 mg/day to 3,500 mg/day of the choline. Nevertheless, the present disclosure is not limited to a specific daily dose of the choline.

In some embodiments, the composition is a food composition for a human and/or a pet such as a companion individual. The food composition may comprise one or more additional substances such as a mineral, another vitamin, a salt, or a functional additive such as flavoring, a colorant, an emulsifier, or an antimicrobial compound or other preservative. Non-limiting examples of suitable minerals include calcium, phosphorous, potassium, sodium, iron, chloride, boron, copper, zinc, magnesium, manganese and iodine. Non-limiting examples of suitable additional vitamins include fat soluble vitamins as A, D, E and K.

In another embodiment, the composition is a pharmaceutical composition comprising one or more pharmaceutically-acceptable carriers, diluents, or excipients. Generally, pharmaceutical compositions are prepared by admixing the omega-3 fatty acid, the nitric oxide releasing compound, and the Vitamin B12 with one or more of an excipient, a buffer, a binder, a plasticizer, a colorant, a diluent, a compressing agent, a lubricant, a flavorant, or a moistening agent.

The composition can have an acute effect that can be seen in less than one month. Additionally or alternatively, the composition can have a long-term effect, and thus various embodiments comprise administration of the composition to the individual (e.g., orally) for a time period of at least one month; preferably at least two months, more preferably at least three, four, five or six months; most preferably for at least one year. During the time period, the composition can be administered to the individual at least one day per week; preferably at least two days per week, more preferably at least three, four, five or six days per week; most preferably seven days per week. The composition can be administered in a single dose per day or in multiple separate doses per day.

Any of the embodiments as defined herein, particularly ingredients of the described compositions may be combined with each other, if not otherwise described. This also applies with regard to the features and benefits of the methods and treatments defined herein employing such compositions.

EXAMPLES

Example 1

The following non-limiting example is illustrative of compositions for attenuating cognitive aging in a non-demented individual, in embodiments provided by the present disclosure.

| Ingredient | Dose/Day |
| --- | --- |
| DHA | 770 mg |
| EPA | 700 mg |
| Vitamin B1 (thiamin) | 50 mg |
| Vitamin B2 (riboflavin) | 15 mg |
| Vitamin B3 (niacin) | 25 mg |
| Vitamin B5 (pantothenic acid) | 23 mg |
| Vitamin B6 (pyridoxine) | 18 mg |
| Vitamin B7 (biotin) | 0.15 mg |
| Vitamin B9 (folic acid anhydrous) | 0.4 mg |
| Vitamin B12 (cobalamin) | 0.5 mg |
| Vitamin C | 500 mg |
| Vitamin D | 0.015 mg |
| Vitamin E | 82.6 mg |
| Selenium | 0.08 mg |
| Citrulline | 3000 mg |
| Choline bitartrate | 85 mg |

Example 2

A study will be conducted in which the primary objective is to demonstrate the efficacy of a 4-year intervention with the compositions set forth in Example 1 to prevent cognitive decline as measured by a composite score of neuropsychological assessments. The total study population will consist of non-demented adults with subjective memory concerns aged 70+ years, with a subgroup of the study population defined by low DHA status (erythrocyte omega 3 index<4.8%) at baseline, and another subgroup of the study population with a Clinical Dementia Rating (CDR) of 0.5 at baseline.

Trial design will be a placebo-controlled, double-blind, randomized, multicenter, 2 parallel groups study. The subjects will be randomly allocated to one of two treatment groups (placebo and BPB).

Subjects will be randomized to one of the investigational products: the compositions representative of Example 1 or a placebo product. The active and placebo investigational products are composed of one sachet containing a powdered drink mix to be reconstituted in cold water and two soft gel capsules.

In the compositions representative of Example 1, the soft gel capsules provide DHA and EPA. The powdered drink contains the rest of the active ingredients with auxiliary ingredients (sucrose, flavors and sweeteners).

In the placebo product, the soft gel capsules contain a mix of vegetable oil free of DHA and EPA but with a similar profile in fatty acid as in the active capsules. The powdered drink does not contain any of the active ingredients and is matched for carbohydrate content to the active powdered drink. It is composed of sucrose/starch, polydextrose, proteins, flavors, natural colorant and sweeteners to be as close as possible to the taste, texture and appearance of the active powdered drink.

The investigational product is taken once daily: one powdered drink and two capsules at the same moment of the day.

During the study, participants will not be permitted to take additional dietary supplements containing B-vitamins: Thiamin (B1), Riboflavin (B2), Niacin (B3), Pantothenic acid (B5), Pyridoxine (B6), Biotin (B7), Folic acid (B9), Cobalamin (B12), DHA, EPA.

The primary endpoint will be the change in a composite score of cognitive assessments at 4-years. The composite score combines the scores in the following neuropsychological tests: learning tests, orientation score, Digit Symbol Substitution test, Category Naming Test. The primary outcome will be looked at the 3 groups (total study population; low DHA status, CDR of 0.5 at baseline).

Secondary endpoints supporting the primary objective will also be studied, specifically
(i) treatment effects on plasma nutrient levels and biomarkers (e.g. homocysteine, Red blood cell (RBC) DHA status) related to BPB intervention;
(ii) treatment effects as measured by separate analyses of test outcomes used in the composite score as well as additional neuropsychological test scores: MMSE total score;
(iii) Trail Making Test, Logical Memory Test, Letter Fluency, Stroop Test, and Digit Span;
(iv) treatment effects as measured by changes in CDR-SOB (Clinical Dementia Rating-Sum of Boxes) scores; and conversion rates to mild cognitive impairment (MCI) and dementia;
(v) treatment effects on participant reported outcomes on function and Quality of Life: Cognitive Function Instrument; EQ-5D-5L; and Applied Cognition—Abilities instruments;
(vi) treatment effects in subgroups defined by the following subject characteristics: high plasma homocysteine levels (plasma homocysteine≥12 μmol/L) at baseline, CAIDE (Cardiovascular Risk Factors, Aging and Dementia) risk score at baseline, amyloid positive on amyloid PET scans at baseline, and genotype.

Further in this regard, biomarkers will be measured, specifically (i) MRI-derived total brain and hippocampal atrophy, and total white matter hyperintensities accumulation, Arterial Spin Labeling imaging, Resting State fMRI in a representative subset of the study population (up to 500 subjects per arm); (ii) Amyloid/Tau PET in a representative subset of the study population (up to 500 subjects per arm); and (iii) blood plasma markers, namely plasma BDNF, plasma Aβ40-42 and Tau protein, asymmetric dimethylarginine, homocysteine, plasma inflammatory markers (sCAMs, E-Selectin, TNFalpha, IL1, IL6, IL10, CRP), and plasma markers of oxidative stress (oxidized low-density lipoprotein (oxLDL), F2-isoprostane).

Secondary exploratory endpoints will include physical function (SPPB), frailty (Fried), anxiety and depression (Geriatric Depression Scale (GDS), Neuropsychiatric inventory questionnaire (NPI-Q)), collect and bank blood and Deoxyribonucleic Acid (DNA) for future research; and effect modification by genetic (single nucleotide polymorphisms e.g., ApoE-ε4, MTHFR, CBS, FAD1/2, other specific genes identified through novel scientific discoveries) or medical (disease states, e.g. diabetes, cardiovascular disease, hypertension).

Example 3—Increase of Membrane Fluidity

The following non-limiting example is an experimental example supporting the use of compositions defined herein to increase membrane fluidity in cultured human induced-pluripotent stem cell derived neurons.

Neurons and Molecular Reagents

Human induced-pluripotent stem cell derived neurons and accompanying growth media were purchased from Cellular Dynamics International. Neurons were cultured according to the manufacturer's protocol (Cellular Dynamics International). Neurons were plated at a density of 100,000-150,000 cells/cm$^2$ in culture vessels (96-well plate μ-clear, Greiner), which have been coated with PLO/Laminin according to the manufactures protocol and maintained in an incubator (37° C., 5% $CO_2$). 50% of the maintenance media was exchanged twice per week.

Two weeks after plating cells have been treated for 24 hours with: DHA+EPA, (15 μM each); B6+B9, (200 μM and 100 μM); B12, (0.05 μM); citrulline, (150 μM); choline, (300 μM); T4 containing DHA+EPA+B6+B9+B12, (15 μM, 15 μM, 200 μM, 100 μM, 0.05 μM); T6low containing DHA+EPA+B6+B9+B12low+citrulline, (15 μM, 15 μM, 200 μM, 100 μM, 0.0005 μM, 150 μM); and T6high (DHA+EPA+B6+B9+B12high+citrulline), (15 μM, 15 μM, 200 μM, 100 μM, 0.05 μM, 150 μM) and control treatments (DMSO 1%, H2O 1% or media only).

After 24 hours the membrane fluidity assay was performed according to the manufactures protocol (Abcam; ab189819). In short, the cells were incubated for 20 minutes at 37° C. with fluorescent lipid reagent. After 20 minutes incubation, media was removed, washed twice with 200 μl of media and then quickly thereafter the fluorescence was measured (FlexStation Microplate Reader, Molecular Devices). After that, the cells were fixed with 4% PFA for 5 minutes at 37° C., washed with PBS. They were then incubated in a solution containing 4',6-diamidino-2-phenylindole (DAPI; 1:50,000 dilution; Sigma Aldrich), a fluorescent stain that binds to DNA and allows for visualization of cell nuclei. Image acquisition was achieved using the ImageXpress (Molecular Devices) platform. Quantification of the total cell count was performed using the MetaXpress software. The total cell count was used to normalize the readout of the membrane fluidity assay.

Data Analyses

Data are presented as box plot (min-max) in FIG. 1. Statistical significance was computed using one-way ANOVA followed by Tukey's multiple-comparison testing. P less than 0.05 was considered significant. As can be seen in FIG. 1 DHA+EPA in combination with high B12 and citrulline (T6$_{high}$) strongly increases membrane fluidity.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A method of attenuating, treating, reducing risk of, and/or reducing severity of cognitive aging in a non-demented individual in need thereof or at risk thereof, the method comprising administering to the non-demented individual a therapeutically effective amount of a composition comprising an omega-3 fatty acid, a nitric oxide releasing compound comprising citrulline, and Vitamin B12, and the composition is administered in a daily dose that provides 50 to 500 times the recommended daily requirement (RDA) of Vitamin B12 per day, wherein the composition comprises one or more additional B vitamins selected from the group consisting of Vitamin B1, Vitamin B2, Vitamin B3, Vitamin B5, Vitamin B6, Vitamin B7 and Vitamin B9.

2. The method of claim 1 wherein the daily dose comprises about 150 to 300 times the RDA of Vitamin B12 per day.

3. The method of claim 1, wherein the non-demented individual is an older adult.

4. The method of claim 1, wherein the non-demented individual is an elderly human.

5. The method of claim 1, wherein the composition is orally administered to the non-demented individual daily for at least one month.

6. The method of claim 1, wherein the omega-3 fatty acid comprises a fatty acid selected from the group consisting of docosahexaenoic acid, eicosapentaenoic acid and mixtures thereof.

7. The method of claim 1, wherein the composition comprises one or more antioxidants selected from the group consisting of Vitamin C, Vitamin D, Vitamin E, selenium and choline bitartrate.

8. The method of claim 1, wherein the non-demented individual has a Clinical Dementia Rating (CDR) of 0.5 at baseline.

9. The method of claim 1, wherein the non-demented individual has a low plasma homocysteine level at baseline of at least 12 µmol/L.

10. The method of claim 1, wherein the non-demented individual has a risk score in Cardiovascular Risk Factors, Aging and Dementia (CAIDE) of 10 to 15 at baseline.

11. The method of claim 1, wherein the non-demented individual is amyloid positive on amyloid PET scans at baseline.

12. The method of claim 1, wherein the non-demented individual has a genotype indicating risk of cognitive decline.

13. A method of attenuating, treating, reducing risk of, and/or reducing severity of cognitive aging in a non-demented individual in need thereof or at risk thereof, the method comprising administering to the non-demented individual a therapeutically effective amount of a composition comprising an omega-3 fatty acid, a nitric oxide releasing compound comprising citrulline, and Vitamin B12, and the composition is administered in a daily dose that provides about 0.4 mg to about 1.0 mg of the Vitamin B12 per day, wherein the composition comprises one or more additional B vitamins selected from the group consisting of Vitamin B1, Vitamin B2, Vitamin B3, Vitamin B5, Vitamin B6, Vitamin B7 and Vitamin B9.

14. A method of achieving one or more of benefits selected from the group consisting of decreasing brain atrophy, increasing or maintaining number of synapses, increasing or maintaining amyloid-β phagocytosis, and decreasing neuroinflammation in a non-demented individual in need thereof, the method comprising administering to the non-demented individual a therapeutically effective amount of a composition comprising an omega-3 fatty acid, a nitric oxide releasing compound comprising citrulline and Vitamin B12, and the composition is administered in a daily dose that provides 50 to 500 times the recommended daily requirement (RDA) of Vitamin B12 per day, wherein the composition comprises one or more additional B vitamins selected from the group consisting of Vitamin B1, Vitamin B2, Vitamin B3, Vitamin B5, Vitamin B6, Vitamin B7 and Vitamin B9.

15. The method of claim 13, wherein the daily dose provides about 200 times the RDA of the Vitamin B12 per day.

16. The method of claim 13, wherein the omega-3 fatty acid comprises a fatty acid selected from the group consisting of docosahexaenoic acid, eicosapentaenoic acid and mixtures thereof.

17. The method of claim 14, wherein the daily dose provides about 200 times the RDA of the Vitamin B12 per day.

18. The method of claim 14, wherein the omega-3 fatty acid comprises a fatty acid selected from the group consisting of docosahexaenoic acid, eicosapentaenoic acid and mixtures thereof.

* * * * *